(12) United States Patent
Al-Maadeed et al.

(10) Patent No.: US 11,551,360 B2
(45) Date of Patent: Jan. 10, 2023

(54) DEVICE AND METHOD FOR CANCER DETECTION

(71) Applicant: QATAR UNIVERSITY, Doha (QA)

(72) Inventors: Somaya Al-Maadeed, Doha (QA); Usman Asghar, Doha (QA); Suchithra Kunhoth, Doha (QA)

(73) Assignee: QATAR UNIVERSITY, OFFICE OF ACADEMIC RESEARCH, Doha (QA)

( * ) Notice: Subject to any disclaimer, the term of this patent is extended or adjusted under 35 U.S.C. 154(b) by 290 days.

(21) Appl. No.: 16/860,579

(22) Filed: Apr. 28, 2020

(65) Prior Publication Data

US 2021/0334969 A1 Oct. 28, 2021

(51) Int. Cl.
*G06T 7/00* (2017.01)
*G01N 33/50* (2006.01)
(Continued)

(52) U.S. Cl.
CPC ......... *G06T 7/0014* (2013.01); *G01N 21/314* (2013.01); *G01N 21/359* (2013.01); *G01N 21/3563* (2013.01); *G01N 33/5005* (2013.01); *G01N 35/00871* (2013.01); *G02B 21/06* (2013.01); *G02B 21/368* (2013.01); *G02F 1/137* (2013.01); *G06K 9/627* (2013.01); *G06T 7/40* (2013.01); *G06V 10/147* (2022.01); *H04N 5/2253* (2013.01); *H04N 5/2254* (2013.01); *H04N 5/2256* (2013.01);
(Continued)

(58) Field of Classification Search
CPC ............... G06T 7/0014; G06V 10/147; G01N 21/314; G01N 21/3563; G01N 21/359; G01N 33/5005; G01N 35/00871; G02B 21/06; G02B 21/368; G02F 1/137
See application file for complete search history.

(56) References Cited

U.S. PATENT DOCUMENTS 6,671,540 B1 12/2003 Hochman
7,522,757 B2 * 4/2009 Tsipouras ........... G01N 15/1475
382/128
(Continued)

FOREIGN PATENT DOCUMENTS

WO WO 01/33229 A1 5/2001

OTHER PUBLICATIONS

High-resolution IR camera with microscope optics; Optris website, Oct. 11, 2017, https://www.optris.com/.
Peyret, et al., "Automactic classification of colorectal and prostatic histologic tumor images using multiscale multispectral local binery pattern texture features and stacked generalization", *Neurocomputing*, vol. 1, No. 11, pp. 1-11; available online May 15, 2017.

*Primary Examiner* — Gregory M Desire
(74) *Attorney, Agent, or Firm* — Squire Patton Boggs (US) LLP

(57) ABSTRACT

A cancer cell detection device includes a computer with a database and a display and a microscope coupled to the computer. The microscope has a base upon which a biopsy sample can be placed. The device further includes a camera coupled to the microscope and computer. The camera is configured to capture images of the biopsy sample. The device also has a filter configured to attach to the microscope and a connection feature for connecting the computer to the camera and the filter. The computer further includes a processor that processes the images captured by the camera and classifies the images according to known variables stored in the database.

17 Claims, 5 Drawing Sheets

(51) Int. Cl.
*G06K 9/62* (2022.01)
*G01N 35/00* (2006.01)
*G01N 21/31* (2006.01)
*G01N 21/359* (2014.01)
*G01N 21/3563* (2014.01)
*H04N 5/225* (2006.01)
*H04N 5/232* (2006.01)
*H04N 7/18* (2006.01)
*G06T 7/40* (2017.01)
*G02B 21/06* (2006.01)
*G02B 21/36* (2006.01)
*G02F 1/137* (2006.01)
*G06V 10/147* (2022.01)

(52) U.S. Cl.
CPC ............ *H04N 5/232* (2013.01); *H04N 7/183* (2013.01); *G01N 2021/3155* (2013.01); *G01N 2021/3166* (2013.01); *G01N 2035/0091* (2013.01); *G02F 2203/055* (2013.01); *G02F 2203/11* (2013.01); *G06T 2207/10048* (2013.01); *G06T 2207/10056* (2013.01); *G06T 2207/30024* (2013.01); *G06T 2207/30096* (2013.01)

(56) References Cited

U.S. PATENT DOCUMENTS

| | | | |
|---|---|---|---|
| 8,185,320 | B2 | 5/2012 | Rimm et al. |
| 8,816,279 | B2* | 8/2014 | Diem ................. H04N 5/33 250/330 |
| 8,937,653 | B2 | 1/2015 | Yamada et al. |
| 8,947,510 | B2* | 2/2015 | Meyer ............ G01N 15/1434 348/E13.074 |
| 9,057,729 | B2 | 6/2015 | Hendriks et al. |
| 9,417,240 | B2 | 8/2016 | Shih et al. |
| 9,495,745 | B2* | 11/2016 | Remiszewski ............ G06T 7/33 |
| 9,622,662 | B2* | 4/2017 | Zuzak ................. A61B 5/0075 |
| 10,123,705 | B2* | 11/2018 | Alfano ................ A61C 19/041 |
| 11,067,787 | B2* | 7/2021 | Christofferson ..... H04N 5/2253 |
| 2006/0184040 | A1 | 8/2006 | Keller et al. |
| 2012/0083678 | A1* | 4/2012 | Drauch ................ A61B 5/0075 702/19 |
| 2013/0242382 | A1* | 9/2013 | Komuro ............ G02B 21/365 359/368 |
| 2017/0053090 | A1 | 2/2017 | Viswanath et al. |
| 2020/0320708 | A1* | 10/2020 | Ma ........................ G06T 7/0012 |
| 2021/0334969 | A1* | 10/2021 | Al-Maadeed ......... H04N 5/232 |

* cited by examiner

DEVICE AND METHOD FOR CANCER DETECTION

FIELD OF INVENTION

The present disclosure is directed to a device and method for detecting cancer cells. More particularly, the present disclosure is directed to an image processing cancer detection system and method.

BACKGROUND

Cancer is one of the deadliest diseases worldwide. Despite all the latest technologies and treatments available, it can be a fatal if not detected timely. The American Cancer society records show that prostate, lung and colon cancers are those leading to highest rates of mortality, and colorectal cancer holds the third position among all other types.

Automated tumor cell grading systems have potential in improving the speed and accuracy of cancer diagnostic procedures. Such systems can boost the confidence level of pathologists who perform the manual assessment of tumor cells. The application of image processing and machine learning techniques on the digitized biopsy slides enables the distinction between various cell types. Deployment of multi-spectral imaging technique for biopsy slide digitization serves to provide spectral information along with the spatial information. Multi-spectral imaging allows pathologists to acquire several images of the sample in multiple wavelengths including the infrared and visible ranges. Current medical imaging techniques deal mostly with images taken in the infrared domain.

In terms of the mortality rate, colorectal cancer holds the third position among all other types. Colorectal cancer can affect the colon, rectum, and parts of the large intestine. Most colon cancers appear initially as colorectal polyps, which are abnormal growths inside the colon or rectum. Among the various diagnostic methodologies available, the major types are colonoscopy, molecular, and histopathologic and spectroscopic diagnosis.

Histopathologic diagnosis refers to the microscopic examination of tissue to study the manifestations of disease, and is commonly referred to as a biopsy. It is the ultimate screening aid for majority of cancers. When testing large populations, however, the analysis of numerous biopsy slides by an experienced pathologist can be a time-consuming task. Moreover, the expertise of the concerned pathologist can affect the result of histopathologic analysis. The tedious task of looking under the microscope may result in several false positives and misinterpretations. Thus, there is a need for a computer aided diagnostic system that can detect and classify the various tumor grades, to improve the reliability and rapidity of the screening procedure.

A wide range of image processing based approaches are currently employed as part of automated colorectal diagnosis. The digitization of biopsy slides is the first step in such approaches. Commonly utilized techniques include RGB, HSV, grayscale etc. Multispectral imaging involves capturing images in specific wavelength bands, including the invisible infrared range. Classification of cells in tissue, which includes cancer detection, have already been adopted multispectral imaging methods.

SUMMARY OF THE INVENTION

In one embodiment, a cancer cell detection system includes a microscope with halogen illumination and a microscope base. The system further includes a filter coupled to the microscope. The filter is configured to be tuned to a specified individual wavelength to capture an image. The system also has a camera attached to the filter. The camera is configured to capture images through the filter of a biopsy sample on the microscope base. The system further includes a computer coupled to the camera. The computer having a memory and a processor. The processor is configured to send commands to the camera to capture a plurality of images through the filter from the microscope.

In another embodiment, a computer implemented method of detecting cancer cells in a biopsy sample is provided. The method includes providing a system having a microscope with halogen illumination and a base configured to hold a biopsy sample, a filter configured to attach to the microscope, a camera attached to the filter, and a computer in communication with the camera. The method further includes initializing the system and sending commands to the camera to capture images through the filter from the microscope. The method also includes performing image analysis on the images captured by the camera.

In yet another embodiment, a cancer cell detection device includes a computer with a database and a display and a microscope coupled to the computer. The microscope has a base upon which a biopsy sample can be placed. The device further includes a camera coupled to the microscope and computer. The camera is configured to capture images of the biopsy sample. The device also has a filter configured to attach to the microscope and a connection feature for connecting the computer to the camera and the filter. The computer further includes a processor that processes the images captured by the camera and classifies the images according to known variables stored in the database.

BRIEF DESCRIPTION OF THE DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION

The disclosed system is described in the context of identifying cancerous cells using an imaging device and imaging processing. While the disclosed system is described with respect to colorectal cancer, it should be understood that it can be extended to any other cancer or dieses which is commonly detected using visual analysis of histopathological specimens. The disclosed method uses a sufficiently large dataset of multispectral colorectal images from prior experiments and incorporates infrared bands. The method applies local phase quantization ("LPQ"). Rotation invariant LPQ features are not known to have not been attempted for cancer cell grading.

The disclosed system and method utilize multi-spectral imaging, which is imaging in individual wavelength bands. In addition, the system and method combines the infrared and visible ranges in the device, thus making it more compact and effective. The system includes image magnifying, image acquisition from camera and multi-spectral filter.

Figure 1:
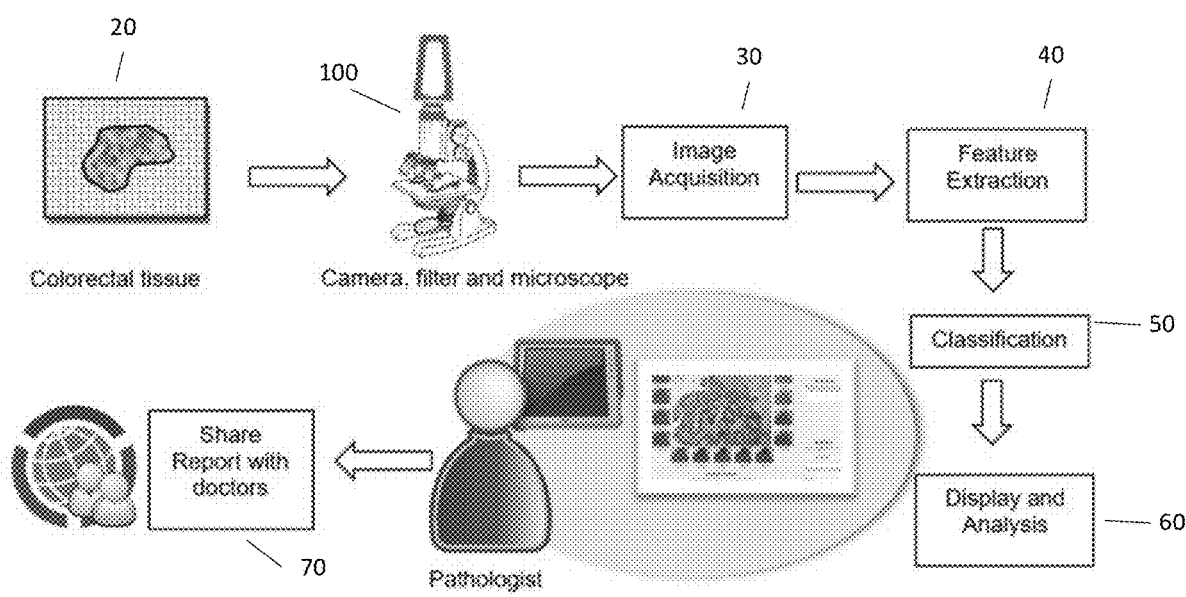
FIG. 1 illustrates an overview of an exemplary process and the described interaction between the system and a user.

FIG. 1 illustrates an overview of the exemplary system 10 and the interaction between the system and a user, such as a pathologist or medical technician. Upon collection, the user places a tissue sample under the microscope 100. An image of the tissue sample 30 is acquired and the system 10 identifies the tissue sample using feature extraction and 40 and classification techniques 50. The results are then displayed on the display panel 60. Upon classification, the medical staff reviews the medical report and discusses treatment. The diagnostic results can be further shared remotely 70.

Figure 2:
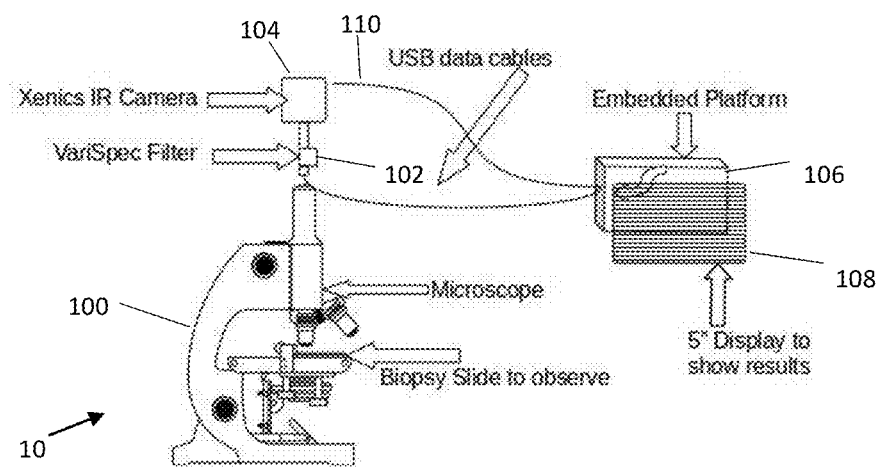
FIG. 2 illustrates a front view of the cancer detection system shown in FIG. 1.

FIG. 2 illustrates an exemplary system 10 for testing a biopsy sample. The system 10 may be located at the same location where the biopsy is performed, or the biopsy sample may be sent from an external location. The system 10 comprises four main elements, a microscope 100, a filter 102, a camera 104, and a computer 106 with a display screen 108. In one embodiment, the microscope 100 is an off the shelf microscope with halogen illumination. The type of illumination is significant because the multi/hyper spectral imaging in the infrared range is only possible using halogen lighting. In one embodiment, the camera 104 is a Xenics IR Xeva 5915 camera. In alternative embodiments, other cameras may be employed.

The computer 106 could include a personal computer (PC), laptop, mainframe computer, tablet, or mobile phone. The computer 106 can be directly connected to the camera 104 and filter 102 using data cables 110 or can be connected wirelessly over a network. In the illustrated embodiment of FIG. 1, the display screen 108 is embedded in the computer 106. In an alternative embodiment, one or more display screens may be separate from the computer.

The filter 102 attaches to the microscope 100 using a known fastening means and is located between the camera 104 and the microscope 100. In one embodiment, the filter 102 is a Liquid Crystal Filter (LCF) that is used to tune to each of the individual wavelength bands of the electromagnetic spectrum allowing multi/hyperspectral images to be captured. The filter 102 may be an off the shelf filter.

In one embodiment, the filter 102 attaches to the microscope by screwing the filter 102 on to an adapter (not shown) that is attached to the microscope 100. In another embodiment, the filter 102 attaches to the microscope by snapping the filter 102 on to the microscope 100. A relay lens (not shown) is disposed between the filter 102 and the microscope 100. The relay lens may be an off the shelf relay lens. The relay lens is attached to the adapter and is between the filter 102 and the microscope 100 to prevent vignetting in the images.

The filter is rated to operate in its optimal light range. In the described system, the filter can operate in at least the ultraviolet, visible, near infrared, and long wave infrared ranges. The filter alters the wavelengths of the light at certain frequencies. The user chooses an optimal filer 102 based upon the required light requirements for the respective imaging. The user may also consider bandwidth when selecting a filter 102.

The filter includes a software development kit (SDK) that allows the user to manually adjust the filter, which alters the wavelength of the light. Optical filter designs may use a static band pass. The addition of the LCF variables to the optical filter design allows for greater tuning of the filter by the user. The amount of light transmitted changes sinusoidally as a function of wavelength. The transmitted light adds constructively to the image in the desired bandwidth region and destructively to the image everywhere else in the wavelength range. Typical transmission of light outside the static band passband is 0.01% or less. The LCF components allow the transparent bandwidth region to be shifted throughout the spectral range of the filter without moving parts.

Figure 3B:
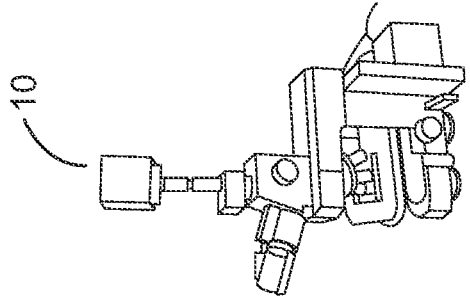
FIG. 3B illustrates a side view of the cancer detection system of FIGS. 1 and 2.
Figure 3D:
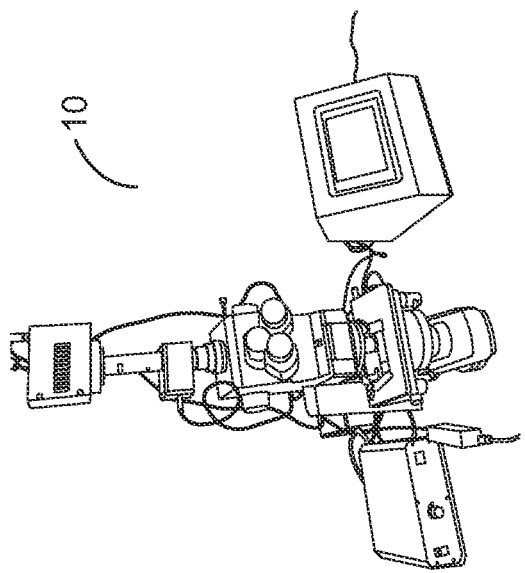
FIG. 3D illustrates one embodiment of a computer, microscope, camera, filter, and display for the camera detection system of FIGS. 1 and 2.
Figure 3A:
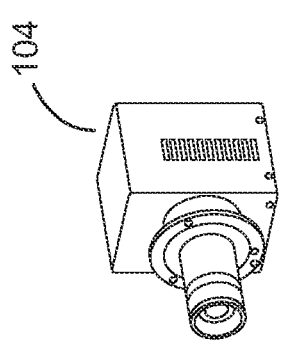
FIG. 3A is a perspective view of one embodiment of a camera for the cancer detection system of FIGS. 1 and 2.
Figure 3C:
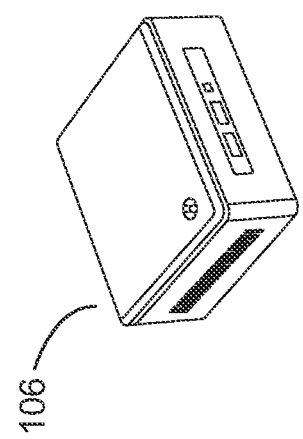
FIG. 3C illustrates a perspective view of one embodiment of a computer for the camera detection system of FIGS. 1 and 2.

FIG. 3A illustrates one embodiment of the camera utilized in the system. The camera 104 attaches to the filter on the opposite end from the microscope 100. The camera 104 attaches to the filter using a known fastening means. In one embodiment, the camera 104 attaches to the filter 102 by screwing the camera 104 on to the filter 102. In another embodiment, the camera 104 attaches to the filter 102 by snapping the camera 104 on to the filter 102. In yet another embodiment, the camera 104 attaches to the filter 102 using the same fastening means as the filter to the microscope.

In one embodiment, the camera 104 is an infrared camera. The camera 104 captures the image of the biological specimens through the microscope 100. The camera 104 can be purchased off the shelf for integration into the system 10. The mount received with the filter 102 allows it to easily connect to the camera through the relay lens. The camera 104 has a viewing range that includes visible light and near infrared light. In one embodiment, the camera 104 has a frame rate of 60 Hz.

After receiving a biopsy sample, the user places the sample on a slide and then places the slide under the microscope 100. The microscope 100 magnifies the micro biopsy slide. The computer 106 sends commands to the camera 104 over the data cables 110, instructing the camera to begin acquiring images. In one embodiment, the computer 106 wirelessly sends commands to the camera 104. The camera 104 will continue capturing images with different wavelengths and storing the captured images in a memory of the computer 106 until a predetermined number of images are captured. The system then analyzes the images.

Figure 4:
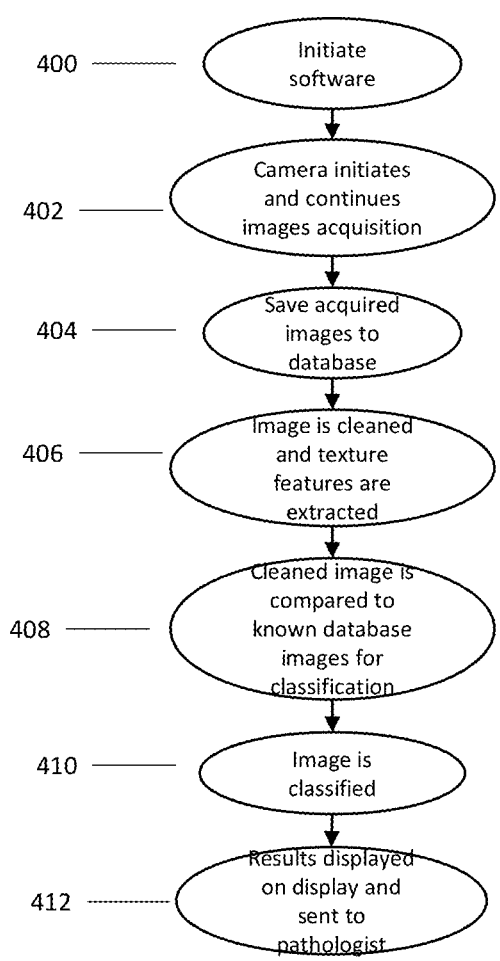
FIG. 4 illustrates a flowchart for detecting cancerous cells utilizing the proposed system.

As shown in FIG. 4, the biopsy slide is placed on the microscope platform and the computer is initialized. The computer 106 then sends a command to the camera 104 indicating how many images to take and instructs the camera 104 to begin taking images 402. The images are stored in the computer. The computer 106 then issues another command to the filter 102 to increase the wavelength band and then initiates the camera 104 to take additional images 402. This process repeats until a desired number of images are captured at different wavelength bands at specified intervals and are saved to the computer 404. In one embodiment, 13 images are captured.

This technique of taking multiple images at different wavelengths is called a multi-spectral method. Once the multispectral images are acquired for a particular biopsy sample, the computer performs images based operations. Such operations include cleaning the image, extracting texture features from the image, and classifying the image using a pre-trained model 406. The computer sends final commands to display the results in the interface and share the information with other doctors and consultants 412.

The number of images to be captured is determined and coded into the computer 106 by the pathologist before the image capture sequence is initialized. The acquired images are stored 406 in a file system on the computer 106. A main directory to the file system is created when the software is installed. Each time a new sequence of images is captured, a new directory within the main directory is created. In one embodiment, the default naming convention for the new directory is by name, current time, and date. There is no requirement for the minimum pixels or size of the images, however, all images should be taken using the same size that the algorithm has been trained to review. This will depend upon the resolution of the camera chosen.

After acquiring and saving the images an image analysis software algorithm will start analyzing the multi-spectral images 406. If there are any unusual glands indicated on the biopsy slide, the output will be projected on the display attached to the computer. The algorithms are loaded onto the computer for image analysis. First, the computer issues a command to acquire the first image from the microscope using the SDK included with the camera and filter. Specialized drivers interact with the SDK of the camera and filter to acquire the image smoothly. Upon acquisition of the image, the computer analyzes all the images from a particular sample and extracts texture features from each image. The extracted texture features from each individual image band are concatenated to form a final feature vector. The final feature vector is compared against known classified data in the database 408. If the final feature vector contains sufficient similarities to the known variables, the biopsy sample is classified accordingly 410.

Figure 5:
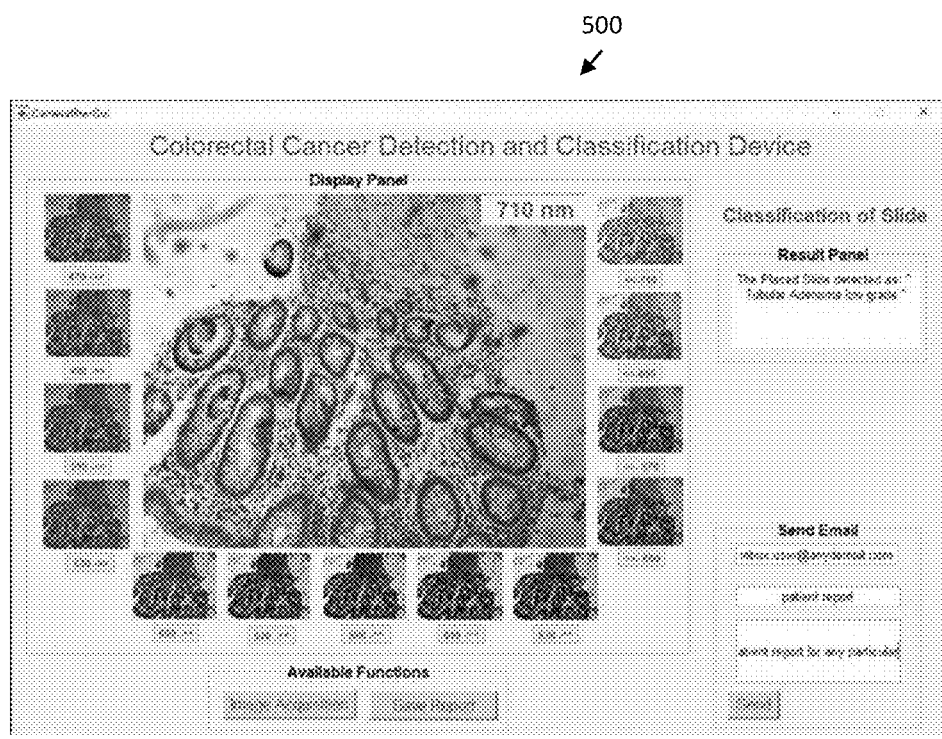
FIG. 5 illustrates one embodiment of the display for the camera detection system of FIGS. 1 and 2.

After the complete compilation of the trained algorithm on multi-spectral images, the computer displays the results 412 including the category of cancer and other related information regarding the sample 500 as shown in FIG. 5. The results are stored as a text file in the same database in which the acquired images for the sample are stored. These results are difficult to achieve and very time consuming if done manually. Using this device expedites the process.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present disclosure has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the disclosure, in its broader aspects, is not limited to the specific details, the representative system and method, and illustrative examples shown and described. Accordingly, departures may be made from such details without departing from the spirit or scope of the applicant's general inventive concept.

What is claimed is:

1. A cancer cell detection system, comprising:
   a microscope with halogen illumination, the microscope having a microscope base;
   a filter coupled to the microscope, wherein the filter is configured to be tuned to a specified individual wavelength to capture an image, and wherein the filter is a liquid crystal tunable filter adaptable to connect to the microscope and the filter further includes a relay lens to prevent vignetting of the images from the microscope;
   a camera attached to the filter, wherein the camera is configured to capture images through the filter of a biopsy sample on the microscope base; and
   a computer coupled to the camera, the computer having a memory and a processor,
   wherein the processor is configured to send commands to the camera to capture a plurality of images through the filter from the microscope.

2. The cancer cell detection system of claim 1, wherein the microscope further includes an adapter for connecting the filter to the microscope.

3. The cancer cell detection system of claim 1, wherein the filter is one of an ultraviolet wavelength filter, visible wavelength filter, near infrared wavelength filter, or long wave infrared wavelength filter.

4. The cancer cell detection system of claim 1, wherein the camera is configured to take images in both visible wavelength and near infrared wavelength.

5. The cancer cell detection system of claim 1 further including a display screen for displaying images.

6. The cancer cell detection system of claim 5, wherein the display screen is embedded on the computer.

7. The cancer cell detection system of claim 1, wherein the computer is directly connected to the camera and filter by data cables.

8. The cancer cell detection system of claim 1, wherein the computer is connected to the camera and filter by a wireless network.

9. A computer implemented method of detecting cancer cells in a biopsy sample, the method comprising:
   providing a system including:
   a microscope with halogen illumination and a base configured to hold a biopsy sample,
   a filter configured to attach to the microscope,
   a camera attached to the filter, and
   a computer in communication with the camera;
   initializing the system;
   sending commands to the camera to capture images through the filter from the microscope; and
   performing image analysis on the images captured by the camera, wherein performing image analysis includes extracting textural features of each image captured by the camera through the filter; and
   concatenating the extracted textural features to form a final feature vector.

10. The computer implemented method of detecting cancer cells in a biopsy sample according to claim 9, further comprising creating a main directory in a file system on the computer and creating within the main directory a storage location for the images captured by the camera.

11. The computer implemented method of detecting cancer cells in a biopsy sample according to claim 9, further comprising sending commands to the camera setting a number of image to be captured by the camera and sending commands to the filter setting a number of various wavelengths.

12. The computer implemented method of detecting cancer cells in a biopsy sample according to claim 11, further including sending a command to set a wavelength in the filter and capture an image through the microscope until the set number of images has been captured by the camera.

13. The computer implemented method of detecting cancer cells in a biopsy sample according to claim 9, further including displaying a classification result.

14. The computer implemented method of detecting cancer cells in a biopsy sample according to claim 9, further including comparing the extracted textural features of the images against known classified data.

15. The computer implemented method of detecting cancer cells in a biopsy sample according to claim 9, further including classifying the biopsy sample upon determining that the images captured by the camera contain sufficient similarities to known variables.

16. The computer implemented method of detecting cancer cells in a biopsy sample according to claim 15, further comprising displaying a category of cancer and other information related to the classified biopsy sample, and storing the category of cancer and other information related to the classified biopsy sample as a text file in a database.

17. A cancer cell detection device, comprising:
 a computer with a database and a display;
 a microscope coupled to the computer, the microscope having a base upon which a biopsy sample can be placed;
 a camera coupled to the microscope and computer, the camera being configured to capture images of the biopsy sample;
 a filter configured to attach to the microscope, wherein the filter is a liquid crystal tunable filter adaptable to connect to the microscope and the filter further includes a relay lens to prevent vignetting of the images from the microscope;
 a connection feature for connecting the computer to the camera and the filter,
  wherein the computer further includes a processor that processes images captured by the camera and classifies the images according to known variables stored in the database.

* * * * *